United States Patent [19]

Ritter et al.

[11] Patent Number: 5,728,313
[45] Date of Patent: Mar. 17, 1998

[54] LEATHER OILING COMPOSITIONS AND THEIR USE

[75] Inventors: Wolfgang Ritter, Haan; Rudolf Zauns-Huber, Duesseldorf; Emil Ruscheinsky, deceased, late of Leverkusen, by Anita Ruscheinsky, executrix; Stefanie Ortanderl, Juechen, all of Germany

[73] Assignee: Henkel Corporation, Plymouth Meeting, Pa.

[21] Appl. No.: 693,072

[22] PCT Filed: Feb. 9, 1995

[86] PCT No.: PCT/EP95/00463

§ 371 Date: Sep. 18, 1996

§ 102(e) Date: Sep. 18, 1996

[87] PCT Pub. No.: WO95/22628

PCT Pub. Date: Aug. 24, 1995

[30] Foreign Application Priority Data

Feb. 18, 1994 [DE] Germany .................. 44 05 205.7

[51] Int. Cl.⁶ .................. C14C 9/02; C14C 1/00; C14C 3/14
[52] U.S. Cl. .......... 252/8.57; 8/94.1 R; 8/94.15; 8/94.18; 8/94.19 R; 8/94.22; 8/94.23
[58] Field of Search .................. 252/8.57; 8/94.15, 8/94.18, 94.19 R, 94.22, 94.23, 94.1 R

[56] References Cited

U.S. PATENT DOCUMENTS

| | | | |
|---|---|---|---|
| 4,701,269 | 10/1987 | Bay et al. | 252/8.57 |
| 4,755,187 | 7/1988 | Friese et al. | 8/94.23 |
| 5,124,181 | 6/1992 | Schaffer et al. | 427/323 |
| 5,279,613 | 1/1994 | Schaffer et al. | 8/94.1 R |
| 5,489,389 | 2/1996 | Ritter et al. | 252/8.57 |
| 5,501,707 | 3/1996 | Schieferstein et al. | 852/94.23 |

FOREIGN PATENT DOCUMENTS

| | | |
|---|---|---|
| 0193832 | 9/1986 | European Pat. Off. . |
| 0213480 | 3/1987 | European Pat. Off. . |
| 0372746 | 6/1990 | European Pat. Off. . |
| 0412389 | 2/1991 | European Pat. Off. . |
| 0418661 | 3/1991 | European Pat. Off. . |
| 0574351 | 12/1993 | European Pat. Off. . |
| 574351 | 12/1993 | European Pat. Off. . |
| 1669347 | 5/1971 | Germany . |
| 4129244 | 3/1993 | Germany . |
| 1591403 | 6/1981 | United Kingdom . |
| WO9401586 | 1/1994 | WIPO . |
| WO9401587 | 1/1994 | WIPO . |

*Primary Examiner*—Anthony Green
*Attorney, Agent, or Firm*—Ernest G. Szoke; Wayne C. Jaeschke; Daniel S. Ortiz

[57] ABSTRACT

A method for oiling leather and skins by impregnating the leather and skins with partial esters of cyclic polycarboxylic acids or (partial) anhydrides with monofunctional fatty alcohols and optionally fixing the partial esters in the leather. Aqueous dispersions or emulsions of the cyclic polycarboxylic and/or (partial) anhydrides partial esters are also disclosed.

22 Claims, No Drawings

LEATHER OILING COMPOSITIONS AND THEIR USE

FIELD OF THE INVENTION

This invention relates to the use of water-dispersible and/or water-emulsifiable partial esters of cyclic polycarboxylic acids or (partial) anhydrides thereof and monohydric alcohols of fatty character as amphiphilic compositions for the oiling and, optionally, retanning of leathers and skins.

BACKGROUND OF THE INVENTION

The oiling of vegetable- and/or mineral-tanned leathers or skins is an essential step in the finishing process leading to the ready-to-use material. The way in which the fats are distributed in the skin and the extent to which the fatty components are bound into the skin critically influence the properties and usefulness of the end products. Extensive expert knowledge exists on possible interactions between the fatty components on the one hand and the tanned skin containing residual tanning agents on the other hand. The particular composition of the oiling compositions, for example the number of lipophilic groups and reactive groups present, if any, for reaction with suitable reactive constituents in the tanned leather, determine inter alia the durability and effectiveness of the oil finish in the practical use of the leather and skin products.

One aspect of practical importance is the provision of oiling compositions which can be so reliably fixed in the tanned skin that the leather and skin products are sufficiently resistant to washing and cleaning for practical requirements. High-quality leather goods, for example from the clothing industry, should be accessible both to washing with detergents and optionally to dry cleaning without any significant loss of quality. In special cases, the oiled leather is also required to be sufficiently waterproof.

RELATED ART

It is known that there are three basic processes for the waterproofing of leather and skins, namely:
1. impregnation by incorporation of water-insoluble compounds, for example solid fats, waxes or special polymers,
2. impregnation by incorporation of water-swelling compounds which, on taking up water, form highly viscous emulsions that block the fiber interstices of the leather, for example special emulsifiers of the w/o type,
3. treatment with hydrophobicizing compounds, for example aluminium, chromium and/or zirconium complexes, silicones or organic fluorine compounds.

DE 1 669 347 describes the use of water-emulsifiable sulfosuccinic acid semiesters for oiling leather, although no waterproofing effects are obtained. EP 193 832 relates to a process for the production of waterproof leathers or skins using sulfosuccinic acid monoesters in combination with impregnating and/or hydrophobicizing oiling compositions, the process being characterized in that, after retanning in aqueous liquor, the leathers or skins are treated with impregnating and/or hydrophobicizing oiling compositions containing sulfosuccinic acid monoester salts with $C_{12-24}$ fatty acid residues and, after acidification, are fixed by addition of a chromium, zirconium and/or aluminum salt. The sulfosuccinic acid monoester salts are preferably used with impregnating oiling compositions from the group of oxidized or oxidized and partly sulfonated $C_{18-26}$ hydrocarbons or $C_{32-40}$ waxes, phosphoric acid mono-$C_{12-24}$-alkyl esters, citric acid mono-$C_{16-24}$-alkyl esters, sorbitan, glycerol and/or pentaerythritol $C_{16-24}$ fatty acid esters.

Amphiphilic compositions in the form of certain selected co-oligomers of, on the one hand, hydrophobic or oleophilic monomers and, on the other hand, hydrophilic monomer constituents have recently been used for the oiling of, in particular, mineral-tanned leathers and skins. Amphiphilic compositions of this type may be incorporated in the leathers or skins to be oiled in the form of aqueous dispersions, emulsions and/or solutions, for example by milling on completion of the main tanning process. In the particular case of mineral-tanned leathers or skins, these amphiphilic compositions may also be used for retanning. Finally, the amphiphilic compositions may be fixed in a concluding step, more particularly with mineral tanning agents. The more recent patent literature describes auxiliaries of the type in question. For example, EP 372 746 describes corresponding compositions and their use, the amphiphilic copolymers being formed from a predominant proportion of at least one hydrophobic monomer and a minor proportion of at least one copolymerizable hydrophilic monomer. The list of hydrophobic monomers mentioned includes long-chain alkyl (meth)acrylates, long-chain alkoxy or alkylphenoxy (polyethylene oxide) (meth)acrylates, primary alkenes, vinyl esters of long-chain alkyl carboxylic acids and mixtures thereof. The hydrophilic comonomers present to a lesser extent are ethylenically unsaturated water-soluble acids or hydrophilic basic comonomers. The molecular weight (weight average) of the copolymers is in the range from 2,000 to 100,000.

EP 412 389 describes compositions for hydrophobicizing leather and skins based on copolymers which have been obtained by radical copolymerization of (a) $C_{8-40}$ monoolefins with (b) ethylenically unsaturated $C_{4-8}$ dicarboxylic anhydrides on the lines of bulk polymerization at temperatures of 80° to 300° C. to form copolymers with molecular weights of 500 to 20,000 g/mole, subsequent solvolysis of the anhydride groups of the copolymers and at least partial neutralization of the carboxyl groups formed during the solvolysis step in aqueous medium with bases and which are present in the form of aqueous dispersions or solutions. EP 418 661 describes the use for the same purpose of copolymers which contain (a) 50 to 90% by weight of $C_{8-40}$ alkyl (meth)acrylates, vinyl esters of $C_{8-40}$ carboxylic acids or mixtures thereof and (b) 10 to 50% by weight of monoethylenically unsaturated $C_{3-12}$ carboxylic acids, monoethylenically unsaturated dicarboxylic anhydrides, semiesters or semiamides of monoethylenically unsaturated $C_{4-12}$ dicarboxylic acids, amides of $C_{3-12}$ monocarboxylic acids or mixtures thereof in copolymerized form and which have molecular weights of 500 to 30,000 g/mole. The copolymers are used for the stated purpose in at least partly neutralized form either as an aqueous solution or as an aqueous dispersion.

Applicants' DE-A41 29 244 relates to the use of aqueous dispersions of co-oligomers from the radical-initiated aqueous emulsion copolymerization at mildly acidic to neutral pH values of
(a) semiesters of maleic acid with oleophilic alcohols and/or lower alkylene oxide adducts thereof and
(b) acrylic acid and/or methacrylic acid
as principal components which may also contain
(c) small quantities of other hydrophilic and/or oleophilic comonomers in the oligomer molecule,
as amphiphilic compositions for the oiling and wash-resistant finishing of leathers and skins.

Applicants' earlier patent application WO 94101587 describes the use of water-dispersible and/or water-emulsifiable co-oligomers of (a) fatty crotonates,
(b) radical-copolymerizable, hydrophilic ethylenically unsaturated acids and/or anhydrides thereof which may also contain
(c) small quantities of other copolymerizable comonomers as amphiphilic compositions for the oiling of leather and skins.

Finally, applicants' earlier application WO 94/1586 describes the use of water-dispersible and/or water-emulsifiable urethane oligomers of fatty character (UR fatty oligomers) containing hydrocarbon/fatty groups together with acid groups capable of salt formation in an at least predominantly uncrosslinked basic structure of the oligomer molecule as amphiphilic compositions for the oiling and, if desired, retanning of leather and skins.

Studies conducted by applicants have shown that comparatively low molecular weights can be crucially important for the rapid and uniform penetration of oiling compositions of the type in question. The polymer chemist can find corresponding indirect references even in some of the documents cited above in the disclosure of the production of the particular copolymer types described therein. The radical copolymerization of the particular components (a) and (b) claimed is said to be best carried out in the presence of chain transfer agents, such as mercaptans (EP 372 746 A2, page 6, 20/21) or in the presence of regulators, such as $C_{1-4}$ aldehydes, allyl alcohol, but-1-en-3-ol, formic acid or organic compounds containing SH groups (EP 418 661 A1, column 6, paragraph 2). The use of corresponding regulators for obtaining polymers of sufficiently low molecular weight is also recommended in EP 412 389, see A1, column 4, paragraph 2.

BRIEF DESCRIPTION OF THE INVENTION

The teaching according to the invention seeks to use for the oiling of leathers and skins a class of amphiphilic compositions which can be exactly determined in advance in regard to their molecular size and molecular weights and which, therefore, enable the interaction with the tanned skin to be optimized. In addition, the class of amphiphilic compositions selected in accordance with the invention and described in the following provides for "fine tuning" of the particular functional components of these amphiphilic compositions. It is thus possible to optimize the various and, in some cases, conflicting requirements, such as high power of penetration into the innermost parts of the tanned skin, but at the same time safe fixing of the oiling composition after introduction, controllable appearance of the oil finish up to and including long-lasting water tightness without the simultaneous formation of a greasy surface.

In a first embodiment, therefore, the present invention relates to the use of water-dispersible and/or water-emulsifiable partial esters of cyclic polycarboxylic adds or (partial) anhydrides thereof and monohydric alcohols of fatty character as amphiphilic compositions for the oiling and, optionally, retanning of leathers and skins.

In this embodiment, the teaching of the invention can be of particular importance for the oiling of mineral-tanned leathers and/or skins, the amphiphilic compositions according to the invention as described above also being capable of performing a retanning function in the course of this oiling treatment.

In another embodiment, the present invention relates to aqueous dispersions of partial esters of cyclic polycarboxylic acids or (partial) anhydrides thereof and monohydric alcohols of fatty character which are adjusted to pH values in the mildly acidic to mildly basic range and which are present as water-dilutable compositions with active-substance contents of at least about 20% by weight and, more particularly, with active-substance contents of around 30 to 70% by weight.

The core of the teaching according to the invention is the use of selected partial esters of, on the one hand, cyclic polycarboxylic acids of the type described hereinafter and, on the other hand, monohydric alcohols of fatty character, these partial esters - by virtue of their content of non-esterified carboxyl groups—being capable of attachment to the skin or of fixing in the skin, more especially with mineral tanning agents, while on the other hand containing hydrocarbon radicals of fatty character predeterminable in regard to type and quantity as ester-forming alcohol radicals in the same molecule. The partial esters are formed or produced by methods known per se, the cyclic polycarboxylic acids, for example, being capable of reaction as such with the ester-forming alcohol components in less than the stoichiometric quantity. However, the cyclic polycarboxylic acids described in detail hereinafter for the production of the amphiphilic compositions according to the invention can often be produced at least partly in the form of their anhydrides and are referred to in the description of the invention as "(partial) anhydrides". In this case, the anhydride ring of the dicarboxylic acid residues in the o-position in the polycarboxylic acid molecule can be opened by ring opening known per se with a monohydric alcohol compound of fatty character, thus developing the amphiphilic character of the partial esters according to the invention.

One important embodiment of the invention uses partial esters of fatty character which are derived from at least tribasic cyclic polycarboxylic acids or (partial) anhydrides thereof. This embodiment of the teaching according to the invention is characterized in that, on average, at least one hydroxyl group per polycarboxylic acid molecule is esterified with the alcohol of fatty character. If desired, however, the ratio of ester groups to carboxyl groups may also be displaced towards larger numbers of ester groups and smaller numbers of free carboxyl groups. Even with an average ratio of two ester groups to one free carboxyl group, the partial esters are sufficiently bound into the structure of the tanned skin.

Taking into account both the availability of corresponding starting components and also the effects to be ultimately established in the leather, suitable cyclic polycarboxylic acids are corresponding 5-membered and/or above all cyclic 6-membered ring systems which—based on the free polycarboxylic acid—contain at least three and preferably at least four free carboxyl groups in the molecule. These carboxyl groups may be at least partly within the ring itself although they may also be attached to the ring as substituents by bridge members.

DETAILED DESCRIPTION OF THE INVENTION

For reasons of industrial availability in particular, but also taking into account the particular oiling characteristics required, suitable polycarboxylic acid components are 6-membered ring systems which may be saturated or olefinically unsaturated, but in particular may even be aromatic in character. This is illustrated by two characteristic examples:

Aromatic polycarboxylic acids containing at least three and preferably four to six carboxyl groups in the $C_6$ ring system are industrially available synthesis units, for example as trimellitic acid or as pyromellitic acid or (partial) anhydrides thereof. The partial esters of these acids can be produced particularly easily by opening the corresponding anhydride rings of adjacent carboxyl groups in the o-position with the alcohol component of pronounced fatty character. Thus, trimellitic anhydride may be reacted with 1 mole of a fatty alcohol or pyromellitic dianhydride may be reacted with 1 mole or with 2 moles of a fatty alcohol. The corresponding partial esters with amphiphilic properties are formed as the reaction product of which the particular molecular size can be determined in advance in accordance with the teaching of the invention.

However, cyclic polycarboxylic acids can also be industrially obtained by other methods, in particular using chemicals based at least partly on natural materials. Monoolefinically unsaturated 6-ring systems, which may be assigned to the group of cyclic polycarboxylic acids defined in accordance with the invention, are formed in known manner by the Diels-Alder reaction of monoolefinically unsaturated mono- and/or polycarboxylic acids or anhydrides thereof with conjugated diolefinically unsaturated components. General expert knowledge of chemistry may be applied in this regard. The following characteristic representatives of cyclic polycarboxylic acids of this type are mentioned purely by way of example:

The fatty acid mixtures derived from oils of vegetable and/or animal origin are generally characterized by high contents of polyunsaturated fatty acids, the representatives containing at least two olefinic double bonds in conjugation to one another being suitable reactants for the known Diels-Alder addition with one other olefinically unsaturated molecule. A typical and industrially accessible example of such "conjuene" fatty acids is ricinene acid which can be a preferred reactant for forming the cyclic polycarboxylic acids and the amphiphilic partial esters derived therefrom. If ricinene acid is reacted with a monoolefinic carboxylic acid and, in particular, a corresponding dicarboxylic acid, a polycarboxylic acid is formed with a monoolefinically unsaturated 6-ring as its core. In the context of the optimization according to the invention, olefinically unsaturated polycarboxylic acids, preferably corresponding dicarboxylic acids, such as maleic acid and/or maleic anhydride (MAH), are particularly suitable as a Diels-Alder reactant with the polyolefinically unsaturated component. Ricinene acid and MAH may be subjected to the Diels-Alder reaction in known manner to form the partial anhydride of a tribasic carboxylic acid which, through further reaction with the monohydric alcohol of pronounced fatty character, becomes the amphiphilic leather oiling preparation corresponding to the teaching of the invention. It is pointed out once again that basic chemical knowledge proves that the description of the history of formation of the cyclic polycarboxylic acids given herein with reference to specific compounds or reactants can be correspondingly modified in various ways. Cyclic polycarboxylic acids are always formed and may be used as an ester-forming reactant for producing the amphiphilic leather oiling preparations according to the invention.

Suitable alcohols for forming the partial esters are selected individual representatives and, in preferred embodiments of the invention, mixtures of various alcohols. The following elements are crucial. The expression "monohydric alcohol of fatty character" encompasses corresponding compounds of natural and synthetic origin. It is known that fatty alcohols of natural origin are obtained by reduction of the associated fatty acids and are generally distinguished by linear chains. However, important embodiments of the invention are characterized by the use or at least the co-use of branched-chain alcohols which, in particular, may be of synthetic origin. The alcohol components may be saturated or, if desired, even olefinically unsaturated. A typical example of an olefinic fatty alcohol of natural origin is oleyl alcohol which may be used to form the amphiphilic partial esters in accordance with the teaching of the invention.

Preferred alcohol components for formation of the partial esters contain 10 to 40 carbon atoms in the molecule, esters based on $C_{12-24}$ fatty alcohols being particularly important. Even in applicants above-cited earlier application WO 94/01587, it is pointed out that, in the context of the oligomer components containing ester groups described therein, the co-use of branched-chain fatty alcohols for ester formation can lead to interesting results in individual cases. For example, through the co-use of branched-chain alcohols, the ability of the amphiphilic compositions to penetrate into the fiber structure of the skin to be oiled can be promoted to a limited extent. It is also possible in this regard to use corresponding branched alcohols with a shorter C chain, corresponding components containing at least 6 carbon atoms and preferably at least 8 carbon atoms being suitable. An important branched-chain alcohol of synthetic origin is 2-ethylhexanol.

In one preferred embodiment of the invention, however, the quantity of branched-chain, more particularly relatively short-chain, alcohols used will be comparatively limited. Thus, generally no more than 50% by weight and preferably no more than 30% by weight or no more than 20% by weight of the total alcohol residues used are formed by such branched-chain and, in particular, lower alcohols. Particularly important representatives for the ester-forming alcohol components can be found in the $C_{12-18}$ range which, in one preferred embodiment, can make up at least about 90 to 95% by weight of the ester-forming alcohol residues.

However, in the context of the teaching according to the invention, the monohydric alcohols of pronounced fatty character are not only the corresponding alcohols in the narrower sense, but also monohydric alcohol derivatives derived therefrom. The following are two characteristic examples: it is known that fatty alcohols can be reacted with lower alkylene oxides, more especially ethylene oxide and/ or propylene oxide, to form corresponding alcohol alkoxylates. Particular significance is attributed in this regard to the alcohol ethoxylates containing an average of at most about 6 EO units per fatty alcohol molecule, corresponding compounds containing 1 to 4 EO units per fatty alcohol molecule being of particular importance. Alkoxylated and, in particular, ethoxylated fatty alcohols with low degrees of ethoxylation which correspond to this definition are also suitable reactants for reaction with the cyclic polycarboxylic acids or their anhydrides for forming the amphiphilic leather oiling compositions according to the invention.

Another characteristic example for modifying the partial esters according to the invention is the use of fatty alcohols extended with lower hydroxycarboxylic acid chains. In this case, too, the degree of chain extension should be limited so that the alcohol component retains its pronounced fatty character. Nevertheless, important properties of the leather or skin treated in accordance with the invention can be controlled by this modification of the fatty alcohol component. For example, the softness of the leather treated with the amphiphilic oiling preparations according to the invention can be distinctly increased by using partial esters of the described type in which long-chain alcohols of natural and/or synthetic origin extended with lactide residues are at least partly used as the ester-forming fatty alcohols. By controlling the average degree of oligomerization of the hydroxycarboxylic acid residues added onto the fatty alcohol and selecting the particular hydroxycarboxylic acids, further modifications and adjustments can be made with a view to optimizing desired product properties. Important hydroxycarboxylic acids for forming corresponding fatty alcohol derivatives are, in particular, the corresponding representatives containing up to 6 and preferably up to 4 carbon atoms, particular significance being attributed to oxalic acid and/or lactic acid for chain extension at the fatty alcohol molecule. Preferred average degrees of oligomerization for the hydroxycarboxylic acid residues introduced are from 1 to 8, preferably from 1 to 5 and more preferably from 1 to 3.

According to the invention, the cyclic partial esters ultimately used are best present in the form of aqueous dispersions and/or emulsions which have preferably been adjusted to a pH value in the mildly acidic to mildly alkaline range. In the interests of storage stability, it can be useful to provide formulations of which the aqueous phase is adjusted to a neutral or mildly alkaline pH value by addition of inorganic and/or organic bases. Any of the bases described in the relevant prior art are suitable for pH adjustment, cf. also the disclosures of the prior art cited at the beginning. The alkali metal salts are preferred, the sodium and/or potassium salts being particularly preferred. However, ammonium salts or salts of alkanolamines, such as diethanolamine, are also suitable representatives. Preferred pH values for storable products may be in the range from pH 7 to 8. It is possible in this way to produce water-containing pastes with a partial ester content of, for example, at least about 20% by weight and preferably from about 30 to 70 or 75% by weight. These pastes may be mixed at any time with water and/or aqueous active-substance mixtures of the type described in the following and used in practice.

One important embodiment of the invention is characterized by the use of amphiphilic compositions of the described type together with selected emulsifiers which, on introduction into leather and/or skins, particularly mineral-tanned leather and/or skins, have an additional oiling or hydrophobicizing effect and, at the same time, can advantageously be fixed in the tanned leather or skin by acid groups. One important example of compounds of this type are the water-emulsifiable sulfosuccinic acid semiesters mentioned at the beginning which originate from long-chain fatty alcohols and/or alkylene oxide adducts thereof. The observations made in the foregoing in connection with the cyclic partial esters apply to the particular character of the alcohols. One important example of emulsifiers belonging to the class in question are $C_{18}$ sulfosuccinate semiesters. It has been found that advantageous effects in the context of the problem to be solved by the invention can be achieved by the co-use of these emulsifier-like auxiliary components which are already known per se as finishes for the oiling of leather. The following are mentioned as examples of compounds of this type: sulfosuccinic acid semiesters of long-chain fatty alcohols containing in particular 12 to 24 carbon atoms and/or alkylene oxide adducts thereof preferably containing up to 6 alkylene oxide residues, corresponding sulfosuccinic acid semiesters of fatty acid monoglycerides and/or diglycerides or alkylene oxide adducts thereof preferably containing up to 6 alkylene oxide residues for a preferred chain length of the fatty acid(s) in the range from $C_{12}$ to $C_{24}$, long-chain sulfofatty acids, more especially corresponding $\alpha$-sulfofatty acids preferably containing 12 to 24 and, more preferably, 16 to 18 carbon atoms, the hydrocarbon radicals normally being saturated in the case of these $\alpha$-substituted sulfofatty acids, and internal sulfofatty acids of monoolefinically and/or polyolefinically unsaturated carboxylic acids, such as oleic acid, linoleic acid, linolenic acid and the like.

However, oiling or hydrophobicizing compositions in the form of the mixtures known from EP 193 832 cited at the beginning may also be used together with the partial esters defined in accordance with the invention. In this embodiment of the invention, therefore, the partial esters of cyclic polycarboxylic acids defined in accordance with the invention combined with impregnating and/or hydrophobicizing oiling agents, such as sulfosuccinic acid monoester salts with $C_{12-24}$ fatty residues, are used in combination with other impregnating oiling compositions selected in particular from the group of oxidized or oxidized and partly sulfonated $C_{18-26}$ hydrocarbons or $C_{32-40}$ waxes. Other examples of these additional impregnating oiling agents are phosphoric acid mono-$C_{12-24}$-alkyl esters, partial esters of non-cyclic polycarboxylic acids, such as citric acid mono-$C_{16-24}$ alkyl esters, partial esters of polyalcohols, such as sorbitan, glycerol or pentaerythritol $C_{16-24}$-fatty acid esters.

A particularly suitable class of emulsifiers which may be co-used to implement the teaching according to the invention are the N-acylamino acids known from the oiling of leathers and skins, more particularly, the fatty acid sarcosides, for example N-oleoyl sarcosine, described in detail in EP-B1-0 213 480, for example as emulsifiers for introducing silicone oils into leathers and skins. Accordingly, suitable emulsifiers are in particular salts of N-($C_{9-20}$-acyl)-amino acids, particular significance being attributed to corresponding salts of an amino acid containing 2 to 6 carbon atoms substituted by the acyl group of a saturated or unsaturated fatty acid containing 9 to 20 carbon atoms at the amine nitrogen which may additionally be substituted by methyl. Particularly suitable salts of these emulsifiers are, again, alkali metal, ammonium or alkanolamine salts.

Of the N-($C_{9-20}$ acyl)-amino acids, those containing 2 to 4 carbon atoms with the amino group in the $\alpha$-position to the carboxyl group, which may be additionally substituted by a methyl group at the amine nitrogen atom are particularly preferred. Of these, the fatty acid sarcosides of saturated or unsaturated fatty acids containing 9 to 20 and preferably 16 to 18 carbon atoms have a particularly superior effect. The preferred sarcoside is oleic acid sarcoside. In addition, N-stearoyl sarcosine, N-lauroyl sarcosine and N-isononanoyl sarcosine in the form of their alkali metal salts, ammonium salts or salts of mono-, di- or trialkanolamines, more especially with 2 to 4 carbon atoms in the alkanol group, are particularly suitable.

Where active-substance mixtures of the type in question are used, the quantity in which the partial esters of cyclic polycarboxylic acids defined in accordance with the invention are used is preferably at least about 35% by weight, based on the active-substance mixture, and more particularly at least about 50% by weight, again based on the active-substance mixture. In a preferred embodiment, at least about 70 to 80% by weight of the total active-substance mixture to be introduced into the leather or skins to be oiled is based on the partial esters according to the invention.

The partial esters of cyclic polycarboxylic acids in the form of an aqueous dispersion or mixtures with the other components mentioned are introduced into the leather and/or skins to be impregnated in known manner, cf. in particular the disclosures of the publications on comparable products cited at the beginning. Accordingly, only a brief summary is given in the following:

The amphiphilic compositions defined in accordance with the invention are suitable for treatment of tanned skins of all the usual kinds, more especially corresponding material which has been tanned with mineral tanning agents. The tanned skins are normally deacidified before the treatment. They may have been colored or dyed before the treatment. However, they may also be colored or dyed after the treatment according to the invention.

The leather to be impregnated is treated with the dispersions in aqueous liquor, optionally in several stages, for up to a few hours, best at pH values of about 4 to 10 and preferably 5 to 8 and at temperatures of around 20° to 60° C. and preferably 30° to 50° C. The treatment is carried out, for example, by milling in a vat. The quantity of partial ester dispersion required is normally 0.1 to 30% by weight and, more particularly, 1 to 20% by weight, based on the pared weight of the leather or the wet weight of the skins. The length of the liquor is normally 10 to 1,000% and preferably 30 to 150% and, in the case of skins, 50 to 500%.

After the treatment with the aqueous liquor. The pH value of the treatment liquor is displaced into the mildly acidic range by addition of acids. The addition of organic acids, preferably formic acid, is particularly suitable. Preferred pH values are in the range from 3 to 5 and preferably in the range from about 3.5 to 4. If desired, the addition of an acid may be followed by fixing, more particularly with mineral tanning agents, preferably aluminium salts and also other polyvalent mineral salts, for example chromium or zirconium salts.

The following Examples describe first the preparation of co-oligomers suitable for the purposes of the invention and then their use for the oiling of leather in accordance with the invention.

EXAMPLES

Example 1

The reaction of pyromellitic dianhydride with a saturated $C_{18}$ fatty alcohol (Lorol $C_{18}$, a product of Henkel KGaA) is carried out as follows:

87.2 g (0.4 mole) of pyromellitic dianhydride are introduced into a reactor together with 500 g of xylene and 217.6 g (0.8 mole) of the $C_{18}$ fatty alcohol and heated under reflux at 140° C.

The acid value of the starting mixture is 111.5. If the reactants are fully reacted, the acid value is reduced by half. The theoretical acid value is reached after a reaction time of 2 hours.

The xylene is removed from the reaction mixture by distillation. A highly viscous, cream-like product is formed and can be dispersed in approximately three times the quantity of water heated to 80° C. The dispersion solidifies on cooling.

Amphiphilic partial esters of pyromellitic acid with the following fatty alcohols or fatty alcohol derivatives are similarly prepared:

$C_{12}$ fatty alcohol (Lorol $C_{12}$, a product of Henkel KGaA); stable solid dispersion

Example 2

Example 1 is repeated without the solvent xylene. The reactants are introduced into the reactor together and intensively stirred at 140° C.

The theoretical acid value is reached after only 1 hour. On completion of the reaction, a highly viscous cream-like product is obtained and can be dispersed in approximately three times the quantity of water heated to 60° C. with addition of 0.1 mole of ammonia. The dispersion solidifies on cooling.

The following reaction products are similarly obtained. In each case, the reaction time is gauged to reach the theoretical acid value and can be up to 6 hours in length:

$C_{14}$ fatty alcohol (Lorol $C_{14}$, a product of Henkel KGaA); readily dispersible, stable preparation fatty alcohol ethoxylate (Dehydol LS4, a product of Henkel KGaA); stable pudding-like preparation unsaturated fatty alcohol (Ocenol 92/96, a product of Henkel KGaA); pale beige, stable preparation lactide-extended fatty alcohol (Lorol $C_{18}$); cream-like to solid, stable preparation

Example 3

A cyclic polycarboxylic acid or its partial anhydride corresponding to the definition according to the invention is prepared as follows:

A commercially available ricinene fatty acid of particularly high "conjuene" content:

| | |
|---|---|
| 65% by weight | conjugated linoleic acid |
| 26% by weight | linoleic acids (linoleic acid and other unconjugated $C_{18}:2$ acids) |
| 6% by weight | oleic acid |
| 3% by weight | saturated $C_{12-18}$ fatty acids | is reacted with maleic anhydride (MA) in a molar ratio of 1:1 in the presence of 0.03% by weight of sulfur as catalyst. The MA is added dropwise over a period of 30 minutes at 100° C. The temperature which rises to around 150° C. under the effect of the heat generated by the reaction is increased to 200° C. and kept at that level for 2 hours. In other reactions, the reaction mixture is heated for another 2 hours to 220° C. in a subsequent reaction phase.

The polycarboxylic anhydride formed is reacted with the fatty alcohols and fatty alcohol derivatives named in Examples 1 and 2 below, but this time in a molar ratio of 1:1. The reaction time is generally about 3 hours. The reaction is carried out in the absence of a solvent, the reaction being over when the theoretical acid value of the reaction product is (substantially) reached.

The partial esters obtained are neutralized with ammonia. Stable aqueous dispersions with solids contents of 30 to 35% by weight can be prepared in every case.

Example 4

The leather applications and studies described in the following are carried out using a product according to the invention—reaction product of pyromellitic dianhydride and $C_{12}$ fatty alcohol (Lorol $C_{12}$) in a molar ratio of 1:2.

In a first series of tests, upper leather of cowhide is used as the material to be oiled. The procedure is as follows:

| Starting material: | Cowhide wet blue pared Pared thickness about 1.8 mm Percentages based on pared weight Starting pH value about 3.9 | | | |
|---|---|---|---|---|
| Process Step | % By Weight | Product/Remarks | °C. | Running Time in Mins. | pH |
| Washing | '300 | Water | 40 | | |
| | 0.2 | HCOOH Drain off liquor | | 20 | 3.8 |
| Neutralization | 150 | Water | 35 | | |
| | 1 | NaHCO₃ Drain off liquor | | 45 | 4.8 |

-continued

| | | | | | |
|---|---|---|---|---|---|
| Washing | 300 | Water | 55 | 10 | |
| | | Drain off liquor | | | |
| Dyeing | 150 | Water | 50 | | |
| | 0.5 | Dyeing auxiliary* | | 10 | |
| | +1 | Dye | | 30 | |
| Oiling | +5.5 | Active substance acc. to the invention | | 90 | |
| | +1 | HCOOH | | 30 | 3.8 |
| Fixing: | +2 | Chrome tanning agent** | | 30 | |
| | +2 | Chrome tanning agent | | 60 | 3.5 |
| | | Drain off liquor | | | |
| Washing | 300 | Water | 40 | 15 | |
| | | Drain off liquor | | | |
| | 300 | Water | 20 | 15 | |

| Further treatment: | a) hoard up overnight, |
|---|---|
| | b) apply vacuum for 1 minute at 70° C., |
| | c) dry |
| | d) condition, |
| | e) stake. |

The commercial products used are as follows:
*"PELLUPUR 400 N" (a product of Henkel KGaA) is a complex-active, dispersing, levelling dyeing auxiliary
**"BAYCHROM F" (a product of Bayer AG) is an organically masked self-basifying 50% basic chrome tanning agent.

To test the hydrophobicizing effect, the upper leather thus oiled is tested in a "Bally" Penetrometer by method IUP 10 of the International Union of Leather Chemists Associations, Commission for the Physical Testing of Leather ("Das Leder", Vol. 12, 36–40 (1961)).

The test specimens were conditioned for 24 h at 23° C./50% relative air humidity (IUP-3/DIN 53303).

In every case, the degree of compression is 15%. The results obtained (tD=penetration time, % WA=% water absorption after x minutes) are summarized in the following Table:

-continued

| Process Step | % By Weight | Product/Remarks | °C. | Running Time in Mins. | pH |
|---|---|---|---|---|---|
| Washing | 300 | Water | 40 | | |
| | 0.2 | HCOOH | | 20 | 3.8 |
| | | Drain off liquor | | | |
| Neutralization | 150 | Water | 35 | | |
| | 1 | NaHCO$_3$ | | 45 | 4.8 |
| | +2 | NaHCO$_3$ | | 60 | 6.2 |
| | | Drain off liquor | | | |
| Washing | 300 | Water | 55 | 10 | |
| | | Drain off liquor | | | |
| Dyeing | 100 | Water | 50 | | |
| | 1.5 | NH$_4$OH | | 10 | 8.0 |
| | +1 | Dyeing auxiliary* | | | |
| | 3 | Dye | | 45 | |
| Oiling | +7 | Active substance acc. to the invention | | 90 | |
| Retanning | +5 | Veget. tanning agent | | 30 | |
| | +1.5 | HCOOH | | 20 | |
| | +1.5 | HCOOH | | 30 | 3.8 |
| | | Drain off liquor | | | |
| Fixing: | 150 | Water | 40 | | |
| | 0.5 | HCOOH | | 15 | 3.8 |
| | +2 | Chrome tanning agent** | | 30 | |
| | +2 | Chrome tanning agent | | 60 | 3.5 |
| | | Drain off liquor | | | |
| Washing | 300 | Water | 40 | 15 | |
| | | Drain off liquor | | | |
| | 300 | Water | 20 | 15 | |

TABLE 1

| | Thickness | tD After | % WA After Minutes | | | | | | | |
|---|---|---|---|---|---|---|---|---|---|---|
| Ref. | mm | Minutes | 60 | 120 | 180 | 240 | 300 | 360 | 420 | 24 h |
| 1 | 2.01 | ≧24 h | 10 | 14 | 16 | 17 | 19 | 20 | 21 | 24 |
| 2 | 2.05 | ≧24 h | 10 | 15 | 18 | 19 | 19 | 21 | 23 | 25 |
| 3 | 2.03 | ≧24 h | 10 | 14 | 17 | 18 | 20 | 22 | 23 | 25 |
| 4 | 2.06 | ≧24 h | 11 | 13 | 14 | 16 | 18 | 19 | 21 | 23 |
| 5 | 2.02 | ≧24 h | 12 | 14 | 15 | 17 | 19 | 20 | 22 | 24 |
| 6 | 2.05 | ≧24 h | 11 | 13 | 15 | 18 | 19 | 19 | 22 | 25 |
| 7 | 2.02 | ≧24 h | 12 | 14 | 15 | 17 | 18 | 19 | 21 | 24 |
| 8 | 2.07 | ≧24 h | 10 | 11 | 13 | 14 | 16 | 17 | 19 | 21 |
| 9 | 2.06 | ≧24 h | 11 | 12 | 14 | 15 | 17 | 18 | 21 | 24 |
| 10 | 2:04 | ≧24 h | 10 | 13 | 14 | 16 | 18 | 19 | 20 | 22 |

Example 5

Comparable investigations—again using the partial ester of pyromellitic dianhydride and $C_{12}$ fatty alcohol in a molar ratio of 1:1—were carried out on furniture leather of cowhide. The furniture leather starting material, its impregnation with the amphiphilic partial ester according to the invention and the testing of the material obtained (Penetrometer) were as follows:

| Starting material: | Cowhide wet blue, pared |
|---|---|
| | Pared thickness about 1.1 mm |
| | Percentages based on pared weight |
| | Starting pH value about 3.9 |

-continued

| Further treatment: | a) hoard up wet overnight; |
|---|---|
| | b) dry at 50° C.; |
| | c) condition; |
| | d) stake; |
| | e) mill (12 hours); |
| | f) tenter. |

The commercial products used were as follows:
*"PELLUPUR 400 N" (a product of Henkel KGaA) is a complex-active, dispersing, levelling dyeing auxiliary
**"BAYCHROM F" (a product of Bayer AG) is an organically masked self-basifying 50% basic chrome tanning agent.

The testing of the samples under the conditions of Example 4 produced the results set out in Table 2 below:

| Ref. | Thickness mm | tD After Minutes | % WA After Minutes ||||||
|---|---|---|---|---|---|---|---|---|
| | | | 60 | 120 | 180 | 240 | 300 | 360 |
| 1 | 1.21 | 150 | 18 | 22 | 27 | 33 | 35 | 40 |
| 2 | 1.19 | 135 | 19 | 24 | 28 | 31 | 36 | 45 |
| 3 | 1.18 | 130 | 20 | 25 | 29 | 34 | 37 | 49 |
| 4 | 1.22 | 155 | 17 | 22 | 25 | 29 | 32 | 39 |
| 5 | 1.19 | 145 | 21 | 27 | 30 | 32 | 38 | 48 |
| 6 | 1.16 | 140 | 19 | 23 | 28 | 31 | 39 | 42 |
| 7 | 1.15 | 130 | 18 | 25 | 29 | 34 | 39 | 45 |
| 8 | 1.18 | 145 | 20 | 26 | 31 | 38 | 41 | 49 |
| 9 | 1.20 | 160 | 17 | 21 | 24 | 28 | 36 | 40 |
| 10 | 1.17 | 115 | 19 | 23 | 28 | 32 | 38 | 47 |

Washing tests were carried out with the furniture leather treated in accordance with the invention. The leather samples were prepared as follows:

After the leather had been conditioned (DIN 53303), test specimens measuring 10×10 cm were cut out, measured and weighed.

The test specimens were then washed with a phosphate-free detergent (Persil, a product of Henkel KGaA) in water at 60° C. using a domestic washing machine with a normal wash program. They were then dried at room temperature.

After reconditioning (DIN 53303), differences in weight and surface area were determined. The results are set out in Table 3 below:

TABLE 3

| Leather Sample | Difference in Weight | Difference in Surface Area |
|---|---|---|
| 1 | −0.6% | −0.4% |
| 2 | −0.6% | −0.4% |
| 3 | −0.5% | −0.3% |
| 4 | −0.4% | −0.4% |
| 5 | −0.4% | −0.4% |
| 6 | −0.5% | −0.5% |
| 7 | −0.5% | −0.4% |
| 8 | −0.6% | −0.4% |
| 9 | −0.5% | −0.3% |
| 10 | −0.4% | −0.4% |

Finally, in another series of tests, the furniture leather treated in accordance with the invention was subjected to dry cleaning.

After conditioning of the leather (DIN 53303), test specimens measuring 10×10 cm were cut out, measured and weighed.

The test specimens were then dry-cleaned with perchloroethylene in a Böwe machine, aired and dried.

After reconditioning (DIN 53303), the differences in weight and surface area were determined. The results obtained are set out in Table 4 below.

TABLE 4

| Leather Sample | Difference in Weight | Difference in Surface Area |
|---|---|---|
| 1 | −4.1% | −3.7% |
| 2 | −4.9% | −3.9% |
| 3 | −5.2% | −4.9% |
| 4 | −4.5% | −3.8% |
| 5 | −5.1% | −4.2% |
| 6 | −4.7% | −4.3% |
| 7 | −4.3% | −4.0% |
| 8 | −4.8% | −3.9% |
| 9 | −4.9% | −3.6% |
| 10 | −5.2% | −4.1% |

It is claimed:

1. A method for oiling and optionally retanning a substrate comprising at least one member selected from the group consisting of leather and skins which comprises: impregnating the substrate with an aqueous dispersion or emulsion comprising a partial ester formed by reaction of at least one member selected from the group consisting of cyclic polycarboxylic acids and (partial) anhydrides of cyclic polycarboxylic acids with monohydric fatty alcohols.

2. The method claimed in claim 1, wherein the partial esters are formed from at least one member selected from the group consisting of tribasic cyclic polycarboxylic acids and tribasic cyclic polycarboxylic acid (partial) anhydrides having a ring system selected from the group consisting of a saturated ring, an olefinically unsaturated ring, and an aromatic ring.

3. The method claimed in claim 1 wherein the partial ester comprises a partial ester of an aromatic polycarboxylic acid containing 4 to 6 carboxylic groups on a $C_6$ ring system with monohydric fatty alcohols.

4. The method claimed in claim 1 wherein the partial ester comprises the partial ester of cyclic polycarboxylic acids formed by a Diels-Alder reaction of at least one member selected from the group consisting of monoolefinically unsaturated monocarboxylic acids, monoolefinically unsaturated polycarboxylic acids, monoolefinically unsaturated monocarboxylic acid anhydrides and monoolefinically unsaturated polycarboxylic acid (partial) anhydrides with conjugated diolefinically unsaturated compounds.

5. The method claimed in claim 4, wherein the partial esters comprise partial esters of the fatty alcohol with a reaction product of at least one of maleic acid and maleic anhydride with a diolefinically unsaturated monocarboxylic acid.

6. The method claimed in claim 1 wherein the partial esters comprise at least one alcohol group selected from the group consisting of saturated linear $C_8$ to $C_{40}$ alcohols, saturated branched $C_8$–$C_{40}$ alcohols, unsaturated linear $C_8$ to $C_{40}$ alcohols, unsaturated branched $C_8$ to $C_{40}$ alcohols, reaction products of saturated linear $C_8$ to $C_{40}$ alcohols with lower hydroxycarboxylic acids, reaction products of unsaturated linear $C_8$ to $C_{40}$ alcohols with lower hydroxy carboxylic acids, reaction products of saturated branched $C_8$ to $C_{40}$ alcohols with lower hydroxy carboxylic acids, reaction products of unsaturated branched $C_8$ to $C_{40}$ alcohols with lower hydroxy carboxylic acids, reaction products of saturated linear $C_8$ to $C_{40}$ alcohols with lower alkylene oxides, reaction products of linear unsaturated $C_8$ to $C_{40}$ alcohols with lower alkylene oxides, reaction products of branched saturated $C_8$ to $C_{40}$ alcohols with lower alkylene oxides and reaction products of branched unsaturated $C_8$ to $C_{40}$ alcohols with lower alkylene oxides.

7. The method claimed in claim 1 wherein the partial esters comprise partial esters produced by a ring opening of a dicarboxylic anhydride ring with one equivalent of the monohydric fatty alcohol.

8. The method claimed in claim 1 wherein the aqueous dispersion or emulsion comprises the partial esters at a mildly acidic to a mildly alkaline pH value.

9. The method claimed in claim 1 wherein the substrate is impregnated with an emulsion comprising the partial ester and an emulsifier which emulsifier, on introduction into the substrate has an additional oiling effect and can be fixed in a tanned substrate by acidic groups.

10. The method claimed in 1 which further comprises fixing the partial ester impregnated into the substrate by an aftertreatment.

11. The method as claimed in claim 3 wherein the partial ester comprises a partial ester of at least one member selected from the group consisting of pyromellitic acid, and (partial) anhydrides of pyromellitic acid.

12. The method of claim 4 wherein the conjugated diolefinically unsaturated compound contains at least one carboxyl function.

13. The method of claim 5 wherein the diolefinically unsaturated monocarboxylic acid is a conjuene fatty acid.

14. The method of claim 6 wherein the alcohol contains 12 to 24 carbon atoms.

15. The method of claim 10 wherein the partial esters are fixed in the substrate by an aftertreatment of the substrate with a mineral tanning agent.

16. An aqueous dispersion comprising amphiphilic partial esters of at least one member selected from the group consisting of cyclic polycarboxylic acid and (partial) anhydrides of cyclic polycarboxylic acids with monohydric fatty alcohols which dispersion has a mildly acidic to mildly basic pH value and comprises a water-dilutable composition with an amphiphilic partial ester content of at least about 20% by weight.

17. The aqueous dispersion of the amphiphilic partial ester as claimed in claim 16, which additionally contains emulsifiers and optionally leather oiling compositions which contain an oleophilic hydrocarbon group containing at least 8 carbon atoms and at least one acid group.

18. The aqueous dispersion of the amphiphilic partial esters as claimed in claim 16 which contains at least one additional impregnating or hydrophobicizing leather oiling preparation comprising sulfosuccinic acid semiesters with $C_{12-24}$ fatty alcohol residues in combination with at least one compound selected from the group consisting of oxidized $C_{18-26}$ hydrocarbons, oxidized $C_{32-40}$ waxes, oxidized and partly sulfonated $C_{18-26}$ hydrocarbons oxidized and partly sulfonated $C_{32-40}$ waxes, phosphoric acid mono-$C_{12-24}$-alkyl esters, partial esters of polycarboxylic acids, partial esters of polyalcohols, and $C_{18-24}$ fatty acid esters.

19. The aqueous dispersions of the amphiphilic partial esters as claimed in claim 16 wherein the amphiphilic partial esters make up at least about 35% by weight of impregnating and/or hydrophobicizing active substances in the aqueous dispersion.

20. The dispersion of claim 16 containing from 30% to 70% by weight of amphiphilic partial esters.

21. The aqueous dispersion of claim 17 wherein the oleophilic hydrocarbon group contains at least 10 carbon atoms.

22. The aqueous dispersion of claim 17 wherein the emulsifier comprises at least one member selected from the group consisting of sulfosuccinic acid semiesters of long-chain fatty alcohols with 12 to 24 carbon atoms, sulfosuccinic acid semiesters of alkylene oxide adducts of fatty alcohols with 12 to 24 carbon atoms and up to 6 alkylene oxide groups; sulfosuccinic acid semiesters of $C_{12-24}$ fatty acid monoglycerides, sulfosuccinic fatty acid semiesters of alkoxylated $C_{12-24}$ fatty acid monoglycerides having up to 6 alkoxide groups, sulfosuccinic semiesters of $C_{12-24}$ fatty acid diglycerides, sulfosuccinic acid semiesters of alkoxylated $C_{12-24}$ fatty acid diglycerides having up to 6 alkoxide groups, $C_{12-24}$ α-sulfofatty acids, internal sulfonates of monoolefinically unsaturated $C_{12-24}$ fatty acids, internal sulfonates of polyolefinically unsaturated $C_{12-24}$ fatty acids, and salts of a $C_{2-6}$ amino acid substituted by an acyl group of a $C_{9-20}$ fatty acid at an amine nitrogen of the amino acid which may optionally be methyl substituted at the amine nitrogen.

* * * * *